US011688302B2

(12) United States Patent
Ormond et al.

(10) Patent No.: US 11,688,302 B2
(45) Date of Patent: Jun. 27, 2023

(54) NEUROSURGICAL ENDOSCOPY TRAINING DEVICE AND METHOD OF TRAINING

(71) Applicant: The Regents of the University of Colorado, Denver, CO (US)

(72) Inventors: David Ryan Ormond, Denver, CO (US); Jennifer Wagner, Westminster, CO (US); Edin Nevzati, Denver, CO (US)

(73) Assignee: The Regents of the University of Colorado, Denver, CO (US)

(*) Notice: Subject to any disclaimer, the term of this patent is extended or adjusted under 35 U.S.C. 154(b) by 850 days.

(21) Appl. No.: 16/207,376

(22) Filed: Dec. 3, 2018

(65) Prior Publication Data

US 2019/0172370 A1 Jun. 6, 2019

Related U.S. Application Data

(60) Provisional application No. 62/593,759, filed on Dec. 1, 2017.

(51) Int. Cl.
| | |
|---|---|
| *G09B 23/30* | (2006.01) |
| *G09B 23/28* | (2006.01) |
| *G09B 23/34* | (2006.01) |
| *A61B 17/00* | (2006.01) |

(52) U.S. Cl.
CPC ........... *G09B 23/285* (2013.01); *G09B 23/30* (2013.01); *G09B 23/34* (2013.01); *A61B 2017/00707* (2013.01)

(58) Field of Classification Search
None
See application file for complete search history.

(56) References Cited

U.S. PATENT DOCUMENTS

| | | | | |
|---|---|---|---|---|
| 5,620,326 A | * | 4/1997 | Younker | G09B 23/28 434/268 |
| 2014/0051049 A1 | * | 2/2014 | Jarc | G09B 23/30 434/267 |
| 2016/0071437 A1 | * | 3/2016 | Hoke | G09B 23/28 434/267 |
| 2016/0155364 A1 | * | 6/2016 | Piron | G01R 33/58 434/270 |
| 2017/0291359 A1 | * | 10/2017 | Kerins | B33Y 70/00 |
| 2017/0316720 A1 | * | 11/2017 | Singh | G09B 23/285 |

* cited by examiner

*Primary Examiner* — James B Hull
(74) *Attorney, Agent, or Firm* — Snell & Wilmer L.L.P.

(57) ABSTRACT

A neurosurgical endoscopic training system and method for using the system to develop surgical skills and technical competency of an endoscopist. The system includes a portable part-task enclosure with a plurality of walls defining an internal chamber. One of the walls includes an access port coupling the internal chamber to an external environment and the access port can be configured to facilitate the passage of one or more endoscopic surgical tools. The system further includes a plurality of objects disposed within the internal chamber configured for manipulation by a surgical tool that extends through the access port.

14 Claims, 8 Drawing Sheets

NEUROSURGICAL ENDOSCOPY TRAINING DEVICE AND METHOD OF TRAINING

CROSS REFERENCE TO RELATED APPLICATION

This application claims the benefit of U.S. Provisional Patent Application Ser. No. 62/593,579, filed Dec. 1, 2017, which is incorporated herein by reference.

TECHNICAL FIELD

The present invention relates to surgical training, and particularly to a structure for use in learning neuroendoscopic surgical techniques.

BACKGROUND

In recent years, many invasive surgical and operative medical procedures have been developed utilizing endoscopic techniques that can reduce the trauma and recuperative periods associated with prior conventional surgical techniques. Endoscopic procedures have been developed for a wide variety of gynecological, chest, abdominal, joint, and urologic procedures, to place feeding tubes into the digestive tract, to take biopsies, to inspect for tumors, and to correct some types of infertility. These procedures entail inserting instruments, including a video camera, through a small incision into an operative cavity. The video camera is used to guide the surgeon in manipulation of the endoscopic instruments.

Thus, unlike conventional surgical techniques, the surgeon is not able to rely on sense of feel and direct tactile response during an endoscopic surgical procedure and the surgeon's vision is limited to the two-dimensional image viewed through the endoscopic video output, in which many structures may look similar. Depending on the orientation of the endoscopic video camera relative to the organ or other anatomic structure being manipulated, the surgeon may see only an anterior image of the instruments and anatomic structure, or only a posterior image of the instruments and anatomic structure. If is thus critical that surgeons are taught and then maintain endoscopic skills that help them to identify anatomical structures and to carefully control the endoscopic instruments to ensure that a surgical procedure is accurately performed without causing unnecessary damage to surrounding tissues.

A major problem encountered in the development of the above-mentioned surgical processes is the training of surgeons. Performing delicate operations on objects without having the object exposed, i.e., viewing the object through a viewing scope, requires unnatural eye-hand coordination. Thus, it is highly desirable that the skills for performing such surgeries are developed using a simulator. For example, many endoscopic surgeries require suturing and knot tying to close incisions made during surgery. Typically, a double-ended needle secured to the end of a suture thread is manipulated by instruments during suturing. Suturing and knot tying via endoscopy are techniques that require great skill and precision.

Conventional methodologies for teaching endoscopic surgical procedures involve the use of animal specimens. The use of animals for surgical training is very expensive and is found objectionable by many people. Additionally, animal specimens have a short viability on the operating table, and thus provide the trainee with a limited period of time in which to practice repeated techniques.

Surgical training devices called simulators have been developed as alternatives to the use of animals for surgical practice. Earlier models included a transparent panel on top with several openings into which instruments and viewing scope could be inserted and manipulated. Practice "organs" were suspended from the top panel using bead chains and clips. The surgeon could perform practice procedures on living tissues like placenta or muscle.

There thus exists a need for systems and methods to train surgeons in endoscopic techniques that provide low-cost, realistic opportunities to practice endoscopic manipulation and surgical procedures. In order to make this training most effective, trainees should be provided with realistic visual and manipulative feedback during training.

SUMMARY

This disclosure provides a neurosurgical simulator that is enclosed wherein objects for manipulation during training are seen only through a viewing scope so that the surgeon trainee develops eye-hand coordination. The simulator enclosure may house devices for orienting objects within the enclosure to resemble the orientation of a surgical setting. The enclosure may include an opaque cover that includes one or more openings that accommodate the passage of training tools (i.e. surgical instruments) from outside the enclosure, through the enclosure, and into the interior of the enclosure. The surgical instrument training tools are used by the surgeon trainee to manipulate objects in the enclosure to develop the eye-hand coordination required for neurosurgical endoscopy procedures. In particular, the objects for manipulation in the enclosure may be models of brain superstructures, optionally including models of brain pathologies, such as tumors.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Detailed Description and no limitation as to the scope of the present disclosure is intended by either the inclusion or non-inclusion of elements, components, etc. in this Summary. The invention will be more fully appreciated by reference to the following detailed description, drawings, and appended claims.

BRIEF DESCRIPTION OF FIGURES

FIGS. 3A-3F depict multiple objects that may be disposed within the enclosure of the neuroendoscopic simulator of this disclosure for manipulation and training.

FIGS. 4A and 4B depict exemplary structures that can be used to secure objects within the simulator enclosure of this disclosure.

FIGS. 5A-5E depict exemplary neurosurgical-specific objects for manipulation/training within the neuroendoscopic simulator system of this disclosure.

DETAILED DESCRIPTION

Before explaining embodiments of this disclosure in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of this disclosure are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

The present invention relates to devices and system which are useful for training and/or practicing specific neuroendoscopic surgical maneuvers. These devices and system may also be used to objectively assess and train basic neuroendoscopic skills and technical competency.

Different neurosurgical procedures may use endoscopes of different size and functionality. Therefore, the dimensions of embodiments of the device and system of the present disclosure and the associated tasks may be modified to accommodate use of various endoscopes.

Figure 1:
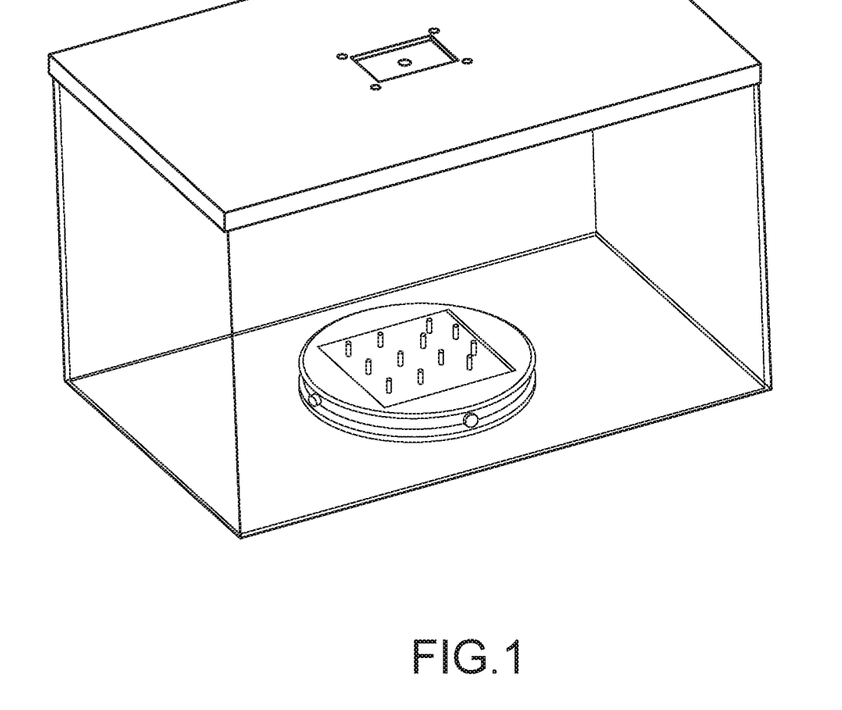
FIG. 1 is a perspective view of an exemplary neurosurgical endoscopic simulator system according to one embodiment of the present disclosure.
Figure 2:
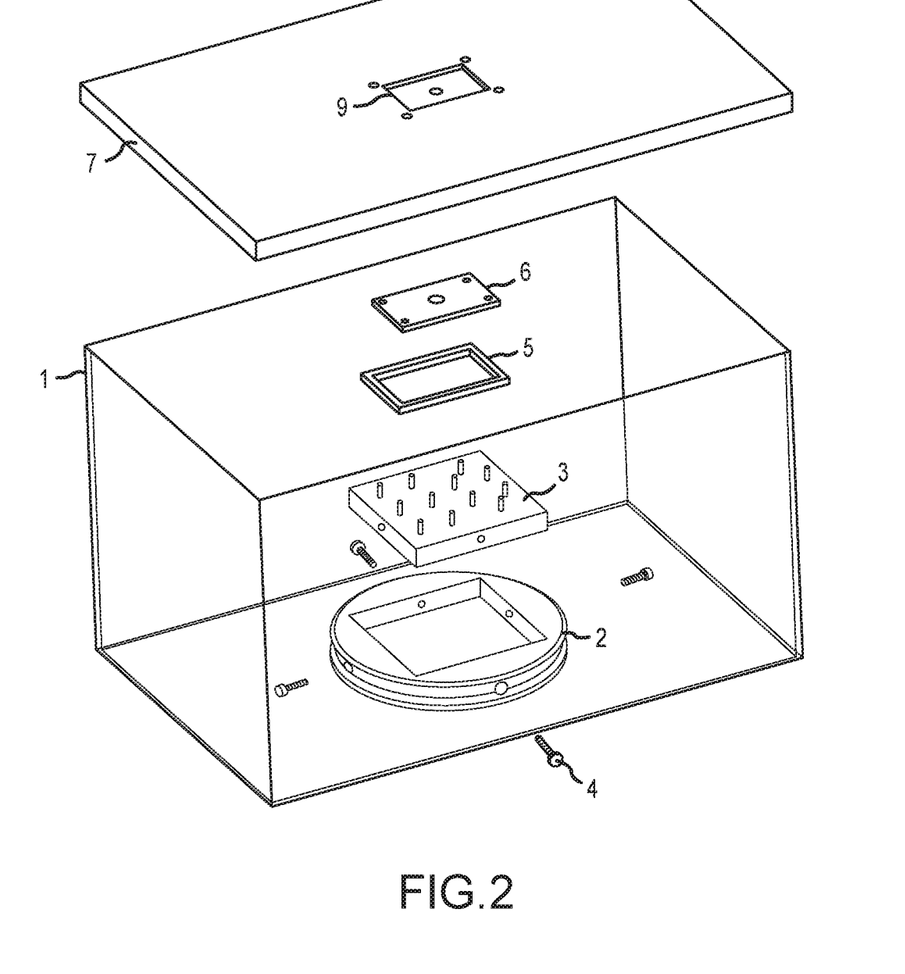
FIG. 2 is an exploded view of the neurosurgical endoscopic simulator depicted in FIG. 1.

FIG. 1 generally illustrates a neurosurgical endoscopic simulator system of this disclosure for individuals such as surgeons or surgeon trainees to learn and practice neuroendoscopic surgical procedures. FIG. 2 illustrates an exploded view of the neurosurgical endoscopic simulator system of FIG. 1. Referring to FIG. 2, the device comprises an enclosure in which objects and tools are deployed to simulate a neurological cavity for neurosurgical endoscopic simulation and training. For the rectangular enclosure 1 depicted in FIG. 2, the top 7 is preferably opaque and includes at least one port 9 providing an opening in the enclosure through which tools or surgical instruments may be passed from outside of the enclosure into the interior of the enclosure. The port 9 may be covered with a covering 6 that is supported by a mounting plate 5. The enclosure 1 includes a mounting structure 2 that position and hold an object 3 intended for manipulation by the surgeon trainee using the neuroendoscopic training system. As depicted in FIG. 2, the object 3 held by the mounting structure 2 may be a pegboard. Set pins 4 may be used to secure the object 3, such as a pegboard, to the mounting structure 2.

The enclosure 1 may be opaque, completely transparent, or semi-transparent. While any suitable enclosure material may be used, the enclosure is preferably composed of a plastic material. Preferably the enclosure is configured to receive and retain liquids such as water for replicating certain neurosurgical procedures during use of the simulator system.

Figure 3A:
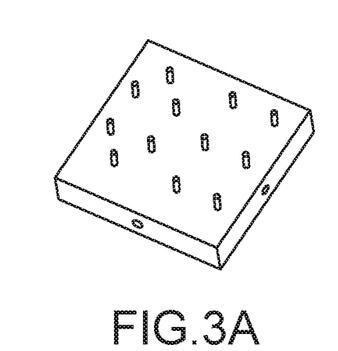
FIG. 3A depicts a perspective view of a pegboard that may be disposed within the enclosure of the simulator to position other objects for manipulation by the surgeon trainee and/or for directly performing training tasks using the simulator of this disclosure.
Figure 3B:
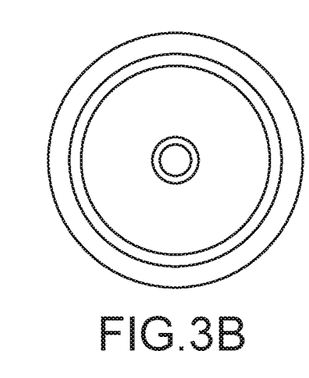
FIG. 3B depicts a bone-simulated object with a small hole in the center meant to simulate antrostomy or other endonasal procedures involving a rangeur on thin bone.
Figure 3C:
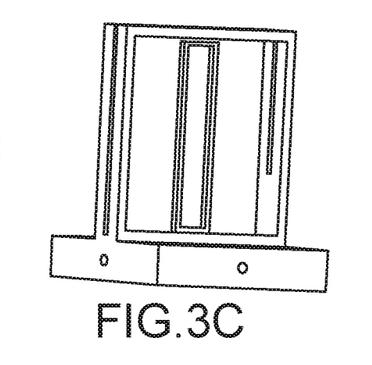
FIG. 3C depicts a perspective view of a simulated nasal septum object.
Figure 3D:
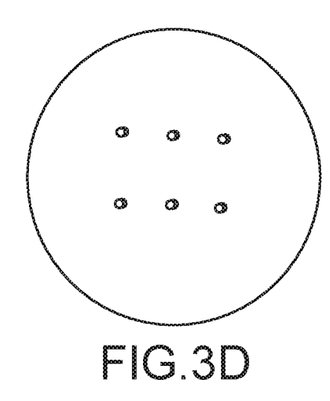
FIG. 3D depicts a simulated endoscopic third ventriculostomy/fenestration task training object.
Figure 3E:
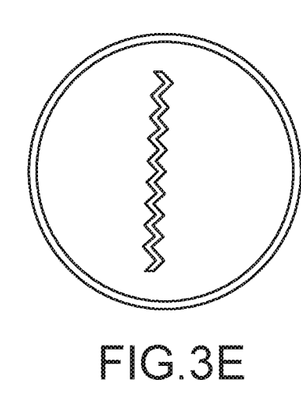
FIG. 3E depicts an object for training a cutting task through a channel.
Figure 3F:
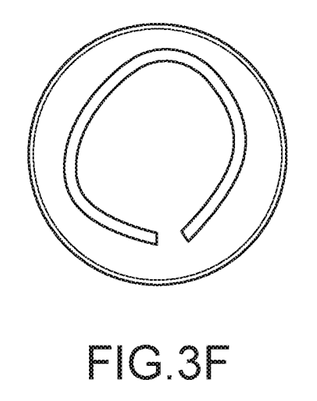
FIG. 3F depicts an object for training a cutting task with multiple instruments (to grasp and cut).

An appropriate sample of body tissue, human or animal, or a synthetic operable structure, can be placed in the enclosure 1, in mounting structure 2, for manipulation by the surgical trainee using the system to train for or practice neuroendoscopic procedures. Referring to FIGS. 3A-3F, many different objects may be placed in the enclosure for manipulation. For example, FIG. 3A depicts a pegboard that may be used to practice a ring transfer task, in which small rubber rings are transferred from, for example, pegs on the left to the six pegs on the right. This task can be completed in an aqueous environment with a working channel endoscope, or with an endoscopic assisted method in an air interface through a simulated nose. If done through the simulated nose, two tools must be used to transfer the ring from one instrument to the other prior to its replacement on the new peg. FIG. 3B depicts a bone-simulated material with a small hole in the center meant to simulate antrostomy or other endonasal procedures involving a rangeur on thin bone. The trainee must expand the os accurately from the original small inner hole to the edge, but not beyond, the outer hole. This requires the use of an endoscopic assisted endoscope in an air environment through a simulated nose. FIG. 3C depicts a simulated nasal septum. The task practiced with this object includes cutting and elevating a silicone membrane from a vertical surface with a dissector. Then, to practice the use of a debrider, the elevated septum is debrided back to a pre-drawn point on the vertical surface. This requires the use of an endoscopic assisted endoscope through a simulated nose in an air environment. FIG. 3D depicts a simulated endoscopic third ventriculostomy/fenestration task that may be repeated a total of six times. At each point, the polyethylene membrane must be fenestrated with a Bugby wire, expanded with either a Fogarty balloon or spreading forceps, and then entered with the endoscopic camera using a working channel endoscope in an aqueous environment. FIG. 3E simulates a cutting task that is performed with a single scissor through a working channel in an aqueous environment. FIG. 3F simulates a cutting task with multiple instruments (to grasp and cut) using endoscopic-assisted techniques through a simulated nose in an air environment.

Figure 4A:
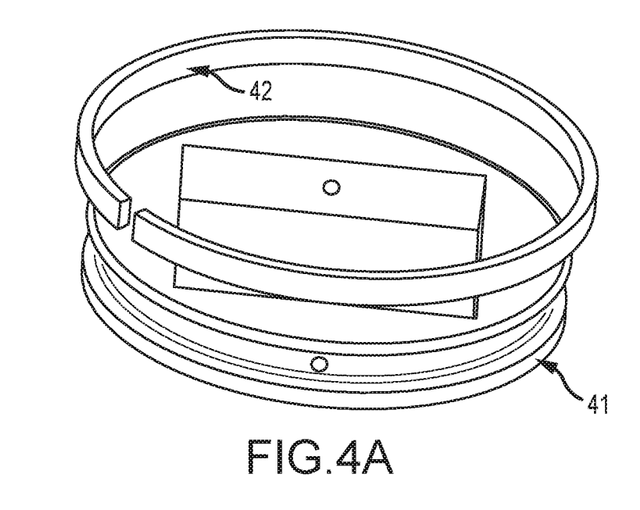
FIG. 4A depicts a structure that can position square or rectangular objects in the enclosure.
Figure 4B:
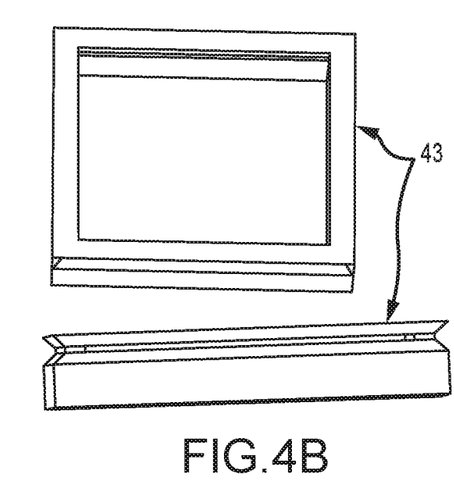
FIG. 4B depicts a structure similar to the structure of FIG. 4A, that can position square or rectangular objects in the enclosure.

FIG. 4A depicts a preferred embodiment of a mounting structure 41 which is formed as a circular structure. To secure objects used for manipulation by the trainee surgeon (such as those depicted in FIGS. 3A-3F) in the enclosure the mounting structure 41 may be contacted with a ring 42 that can be, for example, an elastomeric O ring that slides over and around mounting structure 41 and rests in a groove on mounting structure 41. Alternatively, ring 42 may be an incomplete ring that is tightened using a mechanism, such as a screw or a latch, that draws the ends of the ring together. FIG. 4B depicts a top perspective view (top) and side perspective view (bottom) of a square mounting structure 43. Square objects for manipulation by the trainee surgeon can be secured using a series of set pins (FIG. 2, reference number 4). The set pin holes may be threaded allowing the set pins to secure objects to the mounting structure 43. Examples of other methods for securing objects to the mounting surface may include, but are not limited to, hinges with clamps, screw tightened frames, locking frames, frames with a series of set pins, and magnetic closure devices.

By only being able to view two-dimensional image of the sample on a screen, the trainee is required to operate in an equivalent manner to that necessary in actual laparoscopic surgery. Furthermore, the structure of present invention, having the surgical instruments pass through trocars, cannulas or reducer caps on a flexible membrane, is quite similar to the arrangement used in real endoscopic surgery. Therefore, the present invention thus can provide an opportunity to develop very realistic laparoscopic surgical skills.

Figure 5A:
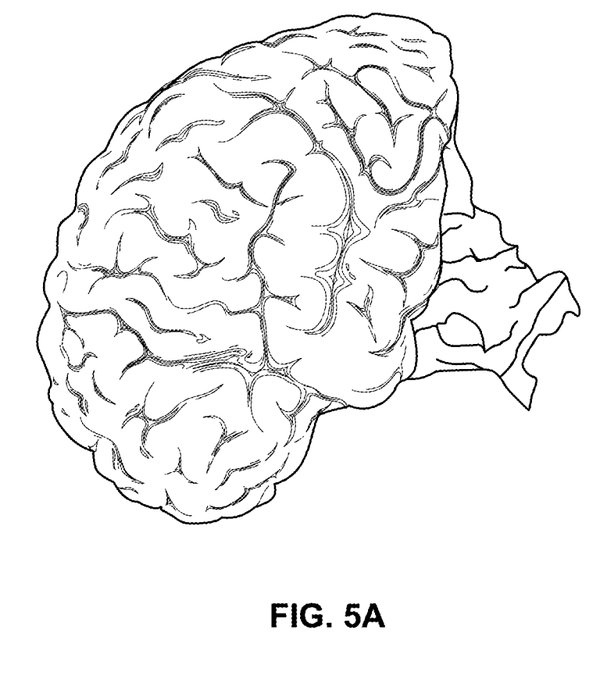
FIG. 5A is a photograph of an elastomeric model of a brain for manipulation/training within the neuroendoscopic simulator system of this disclosure.
Figure 5B:
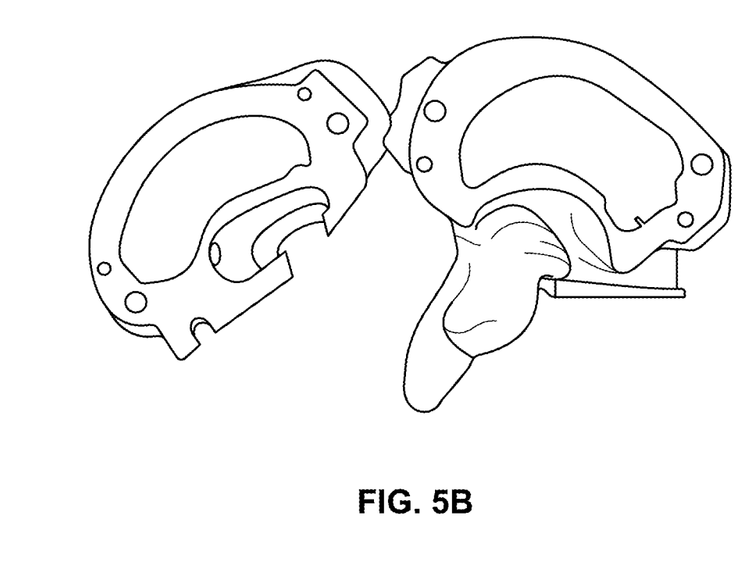
FIG. 5B is a photograph of brain superstructures for manipulation/training within the neuroendoscopic simulator system of this disclosure.
Figure 5C:
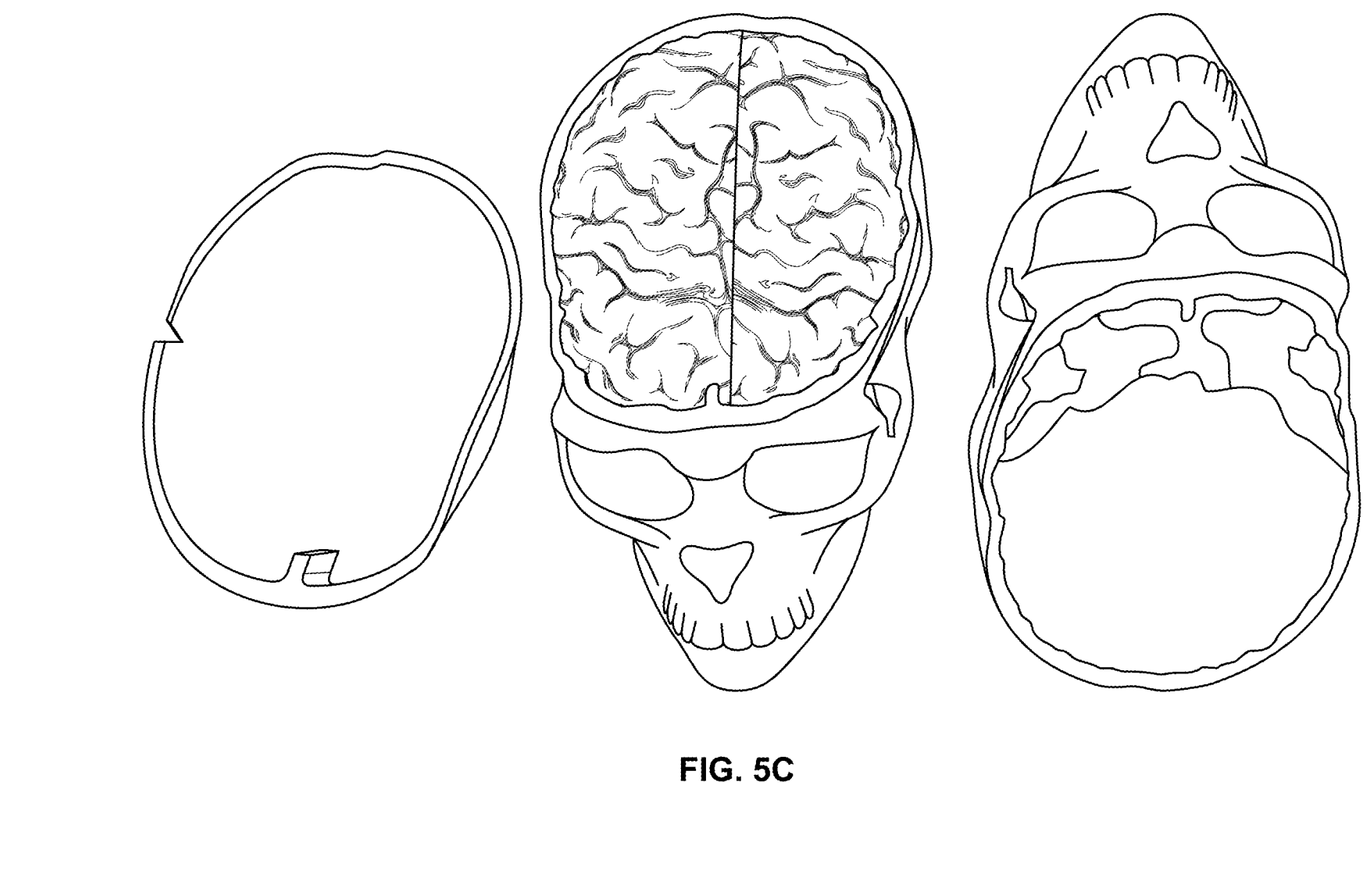
FIG. 5C is a photograph of a human skull model with removable top for manipulation/training within the neuroendoscopic simulator system of this disclosure. As shown, the elastomeric brain model of FIG. 5B may be disposed within the model skull.
Figure 5D:
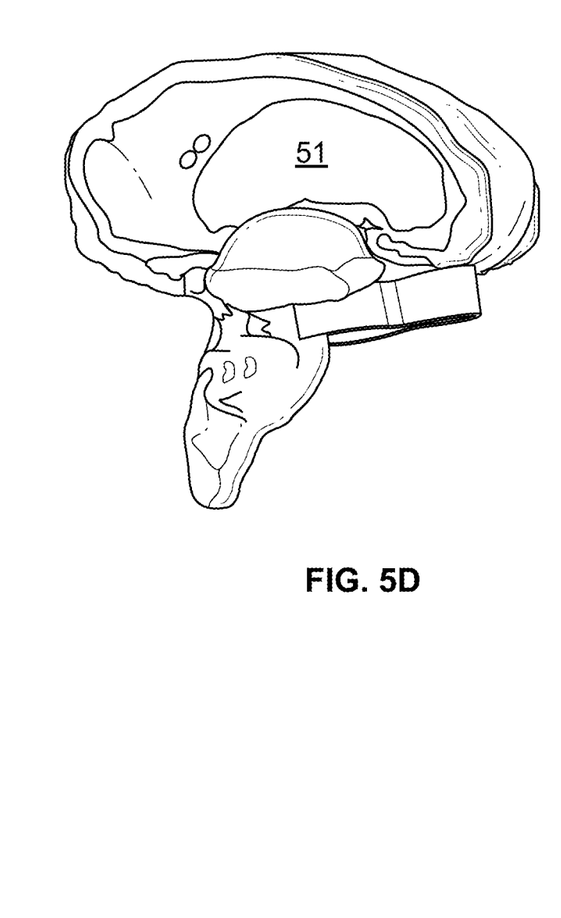
FIG. 5D depicts a brain superstructure model for manipulation/training within the neuroendoscopic simulator system of this disclosure.
Figure 5E:
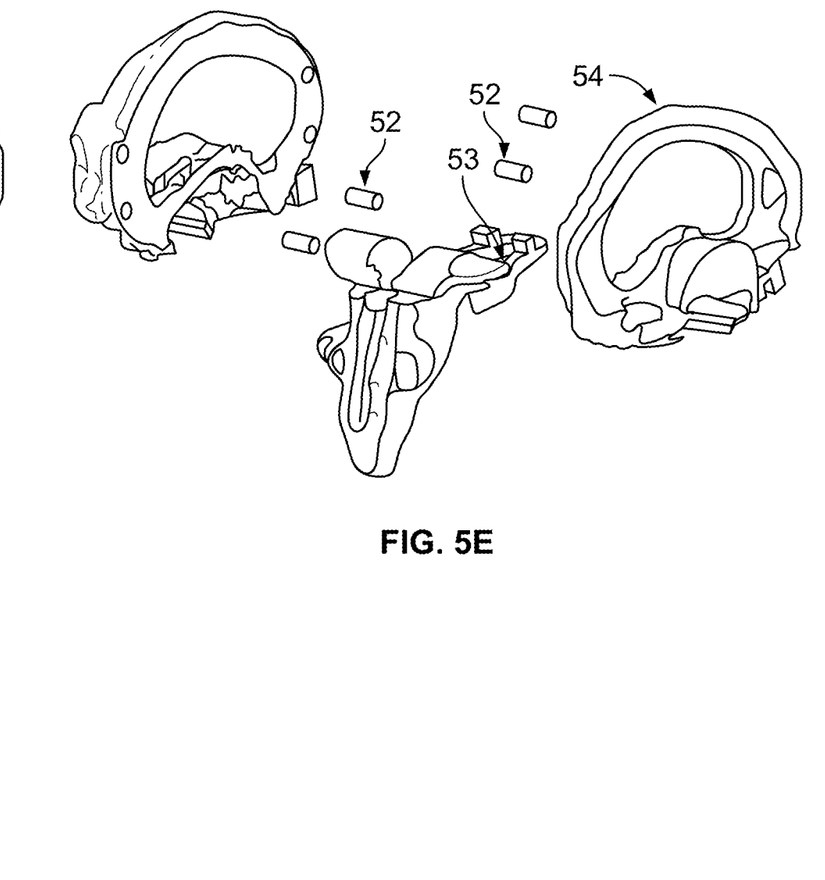
FIG. 5E depicts an exploded view of the components comprising the brain superstructure model of FIG. 5D.

Objects specifically designed for manipulation in training or practicing for neuroendoscopic techniques include elastomeric models of a brain (as shown in FIG. 5A), and/or superstructures of the brain (as shown in FIG. 5B), and/or models of a skull (as shown in FIG. 5C) that may include an elastomeric model of a brain located in the skull (also shown in FIG. 5C). A particularly preferred model of a superstructure of a brain is depicted in FIG. 5D in which a model of an intraventricular septum 51 is formed. FIG. 5E shows an exploded view of the model depicted in FIG. 5D, including set pins 52 that can be used to connect portions of the model. The model of FIG. 5E includes a model of the floor of the third ventricle 53. As depicted in FIG. 5E, these models may include a series of interchangeable pathologies designed to mimic intraventricular tumors, such as meningiomas and colloid cysts 54, depicted in FIG. 5E. These models of brain superstructure may be painted to mimic critical structures such as the basilar artery, choroid plexus, thalamostriate vein, etc. These models of brain abnormalities or pathologies may be connected to the brain superstructure may as desired using, for example, adhesives or mechanical mechanisms including, but not limited to pins, clamps, hook and loop (Velcro™), magnets, and locking channel mechanisms.

Models of cysts and tumors may be composed of, for example, polymeric membranes filled with gelatinous substances designed to mimic human tissues. Similarly, connective tissue can be simulated using textiles or additional polymers.

Figure 6A:
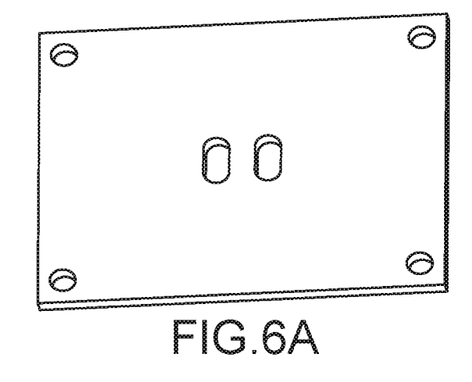
FIGS. 6A-6C depict exemplary coverings for a port formed in the enclosure of the simulator of this disclosure.
Figure 6B:
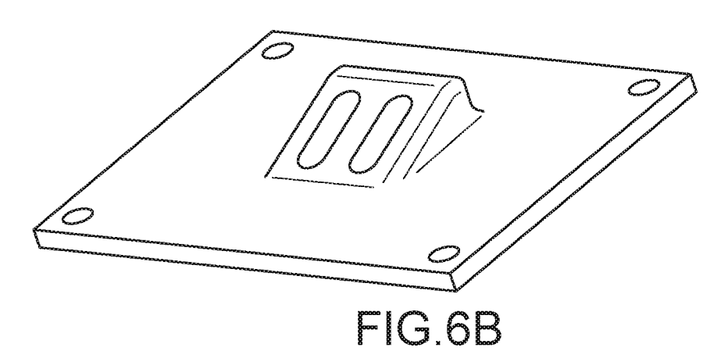
Figure 6C:
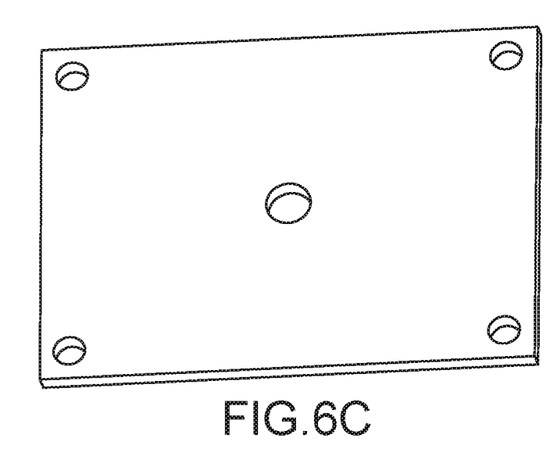

Referring again to FIG. 2, the enclosure top 7 includes a port 9 for the insertion of surgical tools and/or other implements for neurosurgical practice. The port 9 is preferably covered by a covering 6 supported by a mounting plate 5. Referring to FIGS. 6A-6C, the covering is designed to be interchangeable and may be replaced with, for example, any one of the coverings depicted in FIGS. 6A-6C. The covering material is preferably polymeric and designed to provide resistance similar to that encountered during neuroendoscopic procedures. One or more holes may be made in the covering to mimic both trans-nasal and trans-cranial approaches. The covering provides stability for the endoscope and should be opaque, along with the top 7 to prevent surgeon trainees from looking directly at the objects in the enclosure, as opposed to viewing video feed provided by an endoscope deployed in the enclosure. The coverings may be secured to the top 7 over the port 9 using a mounting plate 5 and means to secure the mounting plate 5 and covering 6, such as a series of four screws at each corner of the covering 6. The surface of the mounting plate 5 may be patterned to increase the coefficient of friction between the interchangeable covering 6 and mounting plate 5. The pattern could be saw tooth, random or even a secondary layer applied with adhesive. Surgical instruments passing through the covering 6 models an arrangement used in actual neuroendoscopic surgical procedures, providing the surgeon trainee a very realistic neuroendoscopic surgical skills practice and training system.

Additional optional components may be included in the neuroendoscopy training system of this disclosure to enhance the training or practice experience of the user or to model specific neurosurgical techniques or situations. For example, an augmented reality module may be incorporated as an augmented reality overlay over the surface of the training system to model, for example, pathologies/bleeding scenarios. Blood supply and other fluid systems used to emulate bleeding scenarios and provide fluid pressure feedback features may be included and introduced into the training system. Materials sensitive to ultraviolet light can be used as all or part of the objects deployed in the enclosure for training. Such objects may be used with special neurosurgical microscopes in training scenarios designed to emulate the task of tissue identification and resection. Various cerebral materials may also be used in the training objects to more closely match cerebral tissue. Auditory feedback signals may be incorporated into the training system corresponding to pressure applied by instruments on cerebral materials. This can be accomplished through use of strain gauges, piezo elements, and/or other simple circuitry. Automated image processing algorithms may be used to assess videos captured during training and assign scores.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

What is claimed is:

1. A simulator system for an individual to practice neuroendoscopic surgical procedures, comprising:
    an enclosure comprising (i) an opaque top comprising at least one port allowing passage of surgical instruments from outside the enclosure into an interior of the enclosure and (ii) at least one (1) set pin that is threaded through a pin hole of the enclosure,
    wherein the interior of the enclosure comprises an aqueous environment configured to receive test structures and wherein the interior of the enclosure comprises a mounting structure that is connected to an elastomeric O ring that is configured to slide over the mounting structure;
    a cover covering the at least one port; and
    a test structure formed as a model of a brain superstructure deployed into the aqueous environment within the interior of the enclosure,
    wherein the test structure is secured to the mounting structure using the at least one (1) set pin.

2. The simulator system of claim 1, wherein the enclosure is a rectangular enclosure.

3. The simulator system of claim 1, wherein the test structure is a pegboard used to practice a ring transfer task.

4. The simulator system of claim 1, wherein the enclosure is at least partially filled with water.

5. The simulator system of claim 1, wherein the entire enclosure is opaque.

6. The simulator system of claim 1, wherein the cover covering the at least one port is supported by a mounting plate.

7. The simulator system of claim 1, wherein the mounting structure is configured for holding and orienting the test structure in the enclosure.

8. The simulator system of claim 1, wherein the test structure is selected from the group consisting of:
    a simulated endoscopic third ventriculostomy/fenestration; and
    an object for performing a cutting task with a single scissor through a working channel.

9. The simulator system of claim 1, wherein the test structure is an elastomeric model of a brain.

10. The simulator system of claim 1, wherein the test structure is an elastomeric model of a brain superstructure comprising one or more models of pathologies.

11. The simulator system of claim 10, wherein the pathologies are designed to mimic intraventricular tumors.

12. The simulator system of claim 10, wherein the pathologies are designed to mimic at least one of a meningioma or a colloid cyst.

13. The simulator system of claim 1, wherein the test structure is an elastomeric model of a brain superstructure comprising a brain structure selected from a basilar artery, a choroid plexus, and a thalamostriate vein.

14. A simulator system for an individual to practice neuroendoscopic surgical procedures, comprising:
    an enclosure comprising (i) an opaque top comprising at least one port allowing passage of surgical instruments from outside the enclosure into an interior of the enclosure and (ii) at least one (1) set pin that is threaded through a pin hole of the enclosure,
    wherein the interior of the enclosure comprises an aqueous environment configured to receive test structures and wherein the interior of the enclosure comprises a mounting structure that is connected to an elastomeric O ring that is configured to slide over the mounting structure;
    a cover covering the at least one port; and
    a test structure formed as a model of a brain superstructure deployed into the aqueous environment within the interior of the enclosure, wherein the test structure is secured to the mounting structure using the at least one (1) set pin and wherein the test structure is selected from the group consisting of:
    a bone-simulated material with a small hole in center to simulate endonasal surgical procedures;
    a simulated nasal septum to practice cutting and elevating a membrane from a vertical surface with a dissector; and
    an object for performing a cutting task with multiple instruments to grasp and cut.

* * * * *